United States Patent [19]

Kraus et al.

[11] Patent Number: 4,656,864
[45] Date of Patent: Apr. 14, 1987

[54] FUEL CONTROL SYSTEM FOR INTERNAL COMBUSTION ENGINES

[76] Inventors: Robert A. Kraus; Edmund J. Kraus, both of 1636-T E. Edinger, Santa Ana, Calif. 92705

[21] Appl. No.: 788,634

[22] Filed: Oct. 17, 1985

Related U.S. Application Data

[63] Continuation-in-part of Ser. No. 685,908, Dec. 24, 1985, abandoned.

[51] Int. Cl.$^4$ ............................................. G01N 29/02
[52] U.S. Cl. ........................................ 73/24; 123/494
[58] Field of Search .............. 73/24, 30, 32 A, 861.18, 73/861.02, 861.03; 123/494, 478

[56] References Cited

U.S. PATENT DOCUMENTS

| | | | |
|---|---|---|---|
| 2,703,494 | 3/1955 | Carney | 73/861.02 |
| 2,785,567 | 3/1957 | Poole et al. | 73/24 |
| 3,251,226 | 5/1966 | Cushing | 73/861.18 |
| 3,434,334 | 3/1969 | Vandenbussche | 73/24 |
| 3,557,605 | 1/1971 | Lanneau et al. | 73/24 |
| 3,789,655 | 2/1974 | Passeri | 73/24 |
| 4,009,616 | 3/1977 | Wonn | 73/599 |
| 4,246,773 | 1/1981 | Haruta | 73/24 |
| 4,297,608 | 10/1981 | Jensen | 73/32 A |
| 4,404,859 | 9/1983 | Ohsawa et al. | 73/861.18 |
| 4,561,404 | 12/1985 | Kanno et al. | 123/494 |

Primary Examiner—Stephen A. Kreitman

[57] ABSTRACT

Apparatus for maintaining the correct air/fuel mixture in internal combustion engines. In the preferred embodiment, the density of atmospheric air at concurrent temperature and barometric pressure conditions is sensed by an acoustical transducer whose electric output is electronically correlated with known volumetric flow rate data; thereby obtaining the mass flow rate of engine aspirated air. The acquired air mass flow-rate data, together with other data pertaining to concurrent engine load and condition is utilized to achieve at any throttle position a correct air/fuel ratio. In an alternate embodiment, the mass flow rate of engine aspirated air is obtained by utilizing the basic air density sensing transducer in measuring the suction pressure at the venturi throat within an engine incorporated throttle body device, while simultaneously sensing, and measuring continuously occurring changes in atmospheric conditions.

3 Claims, 5 Drawing Figures

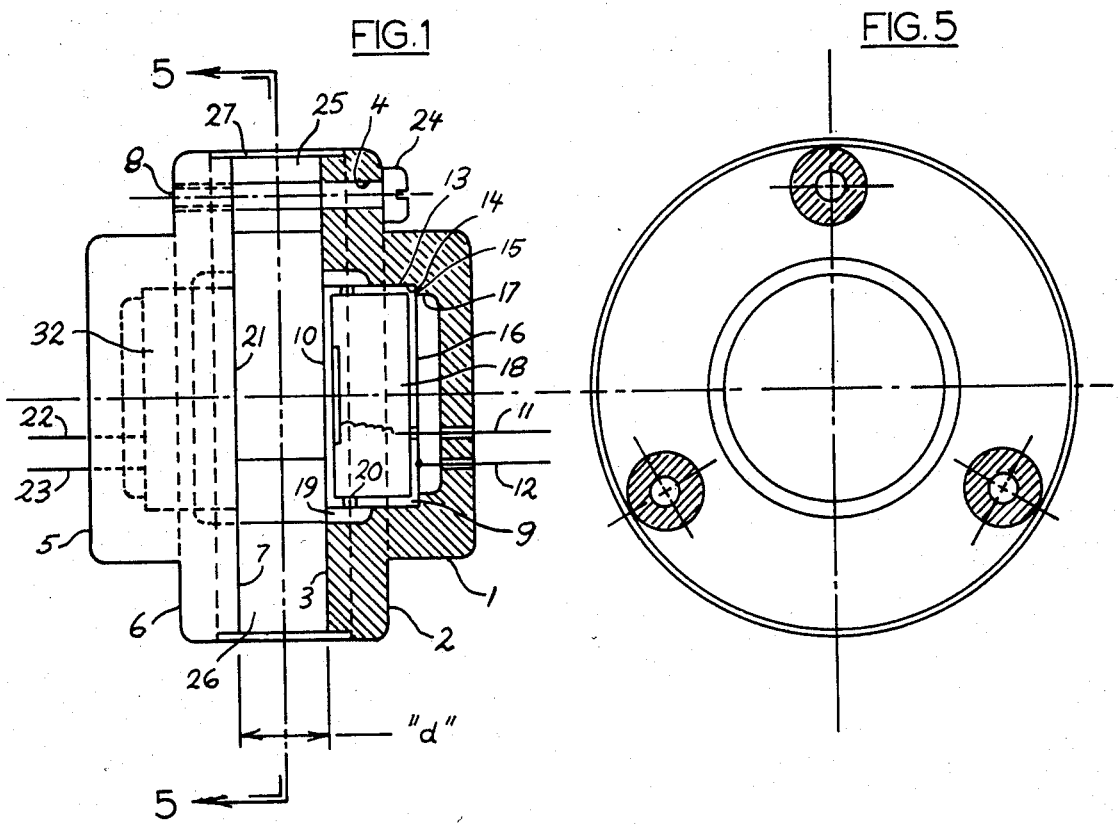
FIG. 1
FIG. 5
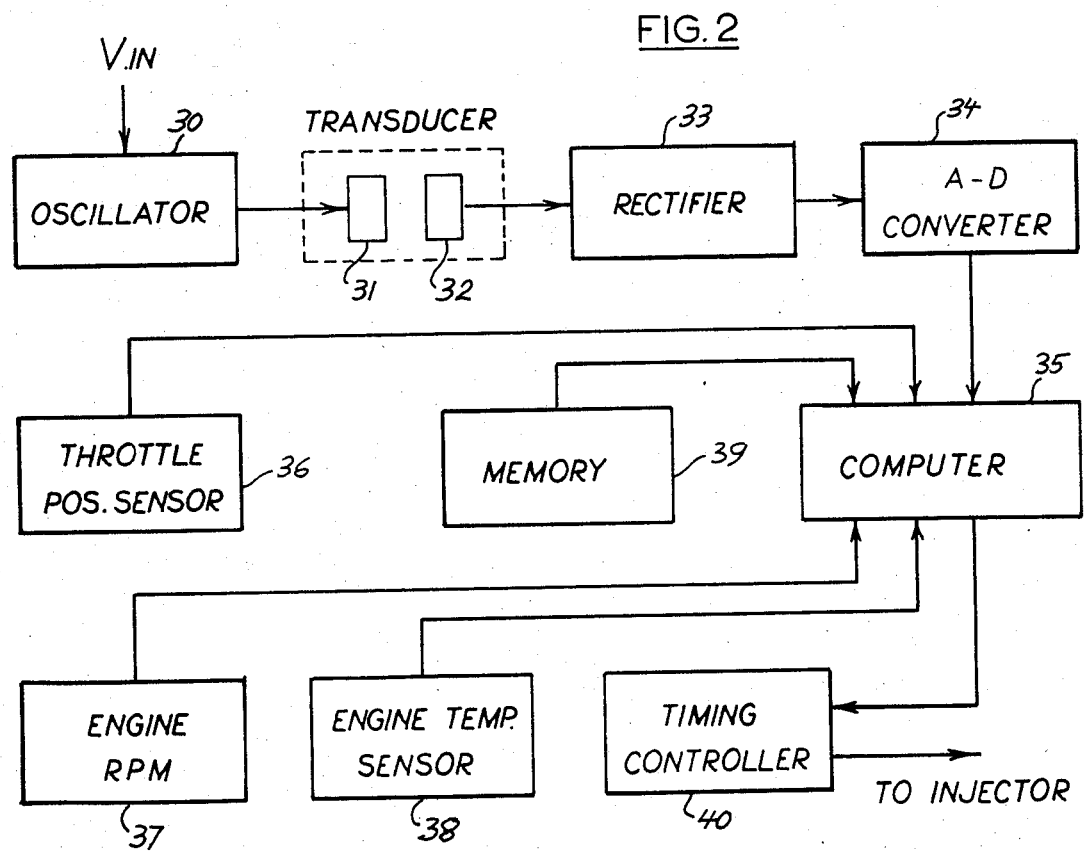
FIG. 2

FUEL CONTROL SYSTEM FOR INTERNAL COMBUSTION ENGINES

This application is a continuation in part of our earlier application with the title GAS-COUPLED TRANSDUCER DEVICE filed in the United States Patent Office on Dec. 24, 1985, having the Ser. No. 06/685,908 which is now abandoned.

BACKGROUND OF THE INVENTION

The present invention relates to an improved engine fuel control systems, and more specifically to a engine fuel control system which compensates for changes in the condition of engine aspirated air due to changes in altitude, atmospheric temperature and/or barometric pressure. Several types of air flow-rate sensing devices as part of engine fuel control systems are known to exist. One of which is described in the U.S. Pat. No. 4,275,695; whose principle of operation utilizes a balanced bridge network in which one branches is a heated wire located within the engine air induction tube. The object of which is to sense the magnitude of air flow variations occurring within the engine air induction tube by measuring the amount of electric current necessary to keep the wire at a constant predetermined temperature. A process, in which the change in the amount of electric current flow within the wire is the consequence of heat exchange from the heated wire to the cooler engine aspirated air. The amount of electric current necessary to keep the wire at its designated temperature is electronically detected, and is conditioned to produce at any given engine load, an electric signal proportional to the rate of air flow through an engine. This, and other engine related data are received and correlated by an automobile on-board computer to maintain at any throttle position a correct air/fuel ratio. While being widely used, the system is characterized by a multitude of shortcomings. Such as for instance, the pulsating of electric current flow within the heated wire caused by the pulsating heat exchange as a consequence of pulsating air flow in step with the opening and closing of the engine intake valves. Or, for instance, the hot wire produced non linear electric output signal. This, and other shortcomings, may have adverse effects on the smooth operation of the engine fuel injection systems. To eliminate such shortcomings, requires, extensive signal conditioning components. Still other limitations may be found in the possible braking, and the formation of unwanted deposits on the heated wire. Another system is described in the U.S. Pat. No. 4,311,042; whose principle of operation, except for the addition of different electronic signal smoothing, and linearizing components is basically as in the heretofore described system, and is therefore subject to basically the same limitations. Still other known devices being described in the U.S. Pat. Nos. 4,457,167 and 4,497,208, mainly deal with the difficult process of smoothening, and linearizing the heated wire produced electric output signal.

SUMMARY OF THE INVENTION

Unlike the air flow measuring devices of the prior art, adopted to measure the rate of air flow expressible in volume per unit time, the fuel control system of the present invention is conceived to utilize the volumetric rate of air flow in conjunction with concurrent atmospheric density to establishing a rate of air flow expressible in mass per unit time. In the preferred embodiment, where electronic data relevant to the volumetric rate of air flow, as well as data provided by the system incorporated throttle position, engine speed and temperature sensors are readily available at the automobile on-board computer, additional data relevant to concurrent atmospheric conditions are provided by the atmospheric density sensing transducer, which together with a computer memory implanted program produces a correct proportionate air/fuel mixture at any engine load, throttle position, and atmospheric condition. The device as set forth in the preferred embodiment utilizes the electronic computer, to continuously calculate the available data such as engine theoretical cylinder displacement, known factor of engine volumetric efficiency, distributor RPM and the atmospheric density in pound per cubic foot; which establishes the mass-flow rate of engine aspirated air. The so obtained mass-flow rate together with additional data relevant to engine throttle position, engine load, and engine condition is correlated by the computer to produce a correct air/fuel ratio according to concurrent operating condition. The device of the present invention as set forth in the alternate embodiment basically utilizes the same fundamental principle of air density sensing as is employed in the preferred embodiment. In the alternate embodiment, the air density sensing transducer measures the suction pressure generated in the conversion of air pressure to velocity within the stream lined constriction within a venturi tube device, while simultaneously sensing deviation in atmospheric conditions. Thereby establishing the mass-flow rate of air expressible mass per unit time. To achieve at any engine load or throttle position the correct air/fuel mixture to be supplied to the cylinders of the engine, it is necessary to provide the automobile on-board computer among the data relevant to the concurrent mass flow rate of engine aspirated air, with additional data relevant to engine throttle position, temperature, and RPM. The fundamental principle of the air density sensing function bases on the change in the magnitude of acoustic energy transmissibility in form of wave motion, (successive pressure pulses) passing along a longitudinal path through the intervening air between sound transmitting and sound receiving piezoelectric elements. Wherein the change in the magnitude of acoustic energy or more specifically, the change in the amplitude of acoustic wave motion at a fixed frequency of preferably no less than 30 KHz arises from the change in the magnitude of air density between sound transmitting and sound receiving elements, from maximum at zero altitude and maximum barometric pressure, to zero at near vacuum conditions. That is to say, the acoustic energy transmissibility follows the natural phenomenon by which sound is most easily transmitted through a gaseous medium at higher density, while no sound may be transmitted through a region being void of gas. Hence, the acoustic energy transmissibility follows any change in air density, either positive, or negative, within a predetermined span.

OBJECTS OF THE INVENTION

It is therefore an object of the present invention to provide low cost means for measuring the mass flow-rate of engine aspirated air without the limitations, characteristic of the prior art.

Another object of the present invention is to provide a low cost means for sensing the density of atmospheric air, specifically intended for combination with a volumetric flow-rate sensing means, to obtain the mass flow-rate of engine aspirated air.

A further object of the present invention is to provide an improved, low cost, and efficient engine fuel management system incorporating mass flow sensing means for engine aspirated air.

A still further object of the present invention is to provide an improved low cost means for sensing the density of atmospheric air, whose produced electric output being utilized in combination with electronically acquired volumetric flow-rate and engine condition data to obtain at any engine load and throttle position the correct air/fuel mixture to be supplied to the cylinders of an internal combustion engine.

The features which are believed to be characteristic of the present invention, both as to their organization and method of operation, together with further objects and advantages will be better understood from the accompanying drawing which we have chosen for purpose of explaining the basic concept of the invention, it is to be clearly understood however, that the invention is capable of being implemented into other forms and embodiments within the scope and spirit of the defining claims by those skilled in the art, which other forms and embodiments will be taken advantage of.

BRIEF DESCRIPTION OF THE DRAWINGS

FIG. 1 represents the partially sectioned view of the basic, acoustical transducer device for sensing the density of atmospheric air.

FIG. 2 represents the block circuit diagram of the electronic components showing the preferred system for controlling the correct air/fuel mixture in internal combustion engines.

FIG. 5 represents a sectional View of FIG. 1, as indicated by 5—5.

DESCRIPTION

Figure 3:
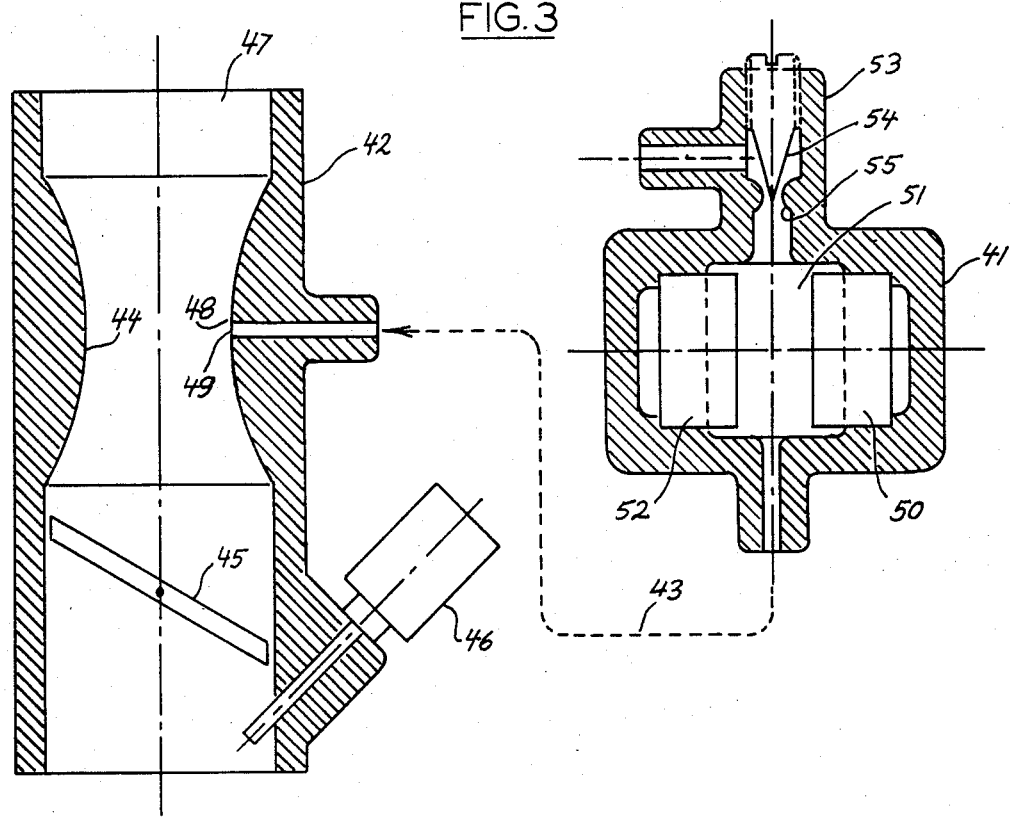
FIG. 3 represents the basic, acoustical air density sensing transducer device being remotely connected to the suction port of a venturi within a throttle body device, so as to form in combination with the venturi, an air mass-flow sensing transducer.

In accordance with the present invention, the atmospheric density sensing transducer assembly in FIG. 1 as adopted in the preferred embodiment comprises the first housing portions 1 having the flange member 2 which is provided with the flat, annular surface 3 and the circumferentially spaced apertures 4. The transducer assembly further comprises the identical, second housing portion 5 having the flange member 6 which is provided with the flat, annular space 7 and the circumferentially spaced, threaded holes 8 being disposed so as to match the geometrical arrangement of apertures 4 on flange member 2. In addition, housing portion 1 comprises the commercially available, acoustic energy generating and propagating piezoelectric, transmitter subassembly 9 having the acoustic wave transmitting surface 10, and the electric input connections 11 and 12. The transducer subassembly is securely fastened via suitable adhesive with its cylindrical outer surface 13 to cylindrical inner surface 14 of housing portion 1, and is disposed, so that its acoustic wave transmitting surface 10 is in a coplanar alignment with the annular surface 3 of flange 2. The proper alignment of which is obtained by resting edge 15 of the transducer subassembly outer end wall 16 against the housing annular ledge 17. To equalize subassembly inner chamber 18 against atmospheric pressure, the annular housing undercut 19 and a series of respective apertures 20 being circumferentially spaced around one end of the subassembly cylindrical wall provides fluid communicative access thereto. Similarly, the second housing portion 5 is provided with the commercially available, acoustic energy receiving and converting piezoelectric transducer subassembly 32 having the acoustically responsive surface 21, and electric output connections 22 and 23. Except for the difference between the apertures 4 of flange 2 and the geometrically matching threaded holes 8 of flange 6, the physical characteristics of both housing portions and their respective transducer subassemblies are in all respects the same. Both housing portions are securely fastened by screws 24 via tubular spacers 25 which are disposed to keep the housing portions separated. To keep dirt and foreign matter from entering space 26 between the transmitting and receiving piezoelectric subassemblies, the fine mesh screen 27 is disposed to cover the devices peripheral opening between housing flanges 2 and 6 so that space 26 remains exposed to atmospheric air. Both, the acoustic energy transmitting surface 10 and the opposite, concentrically thereto disposed, acoustic energy receiving surface 21 are selected to possess the same inherit, natural frequency of vibration. The magnitude of which is in the ultrasonic range. At its resonant frequency surface 21 will respond to minimum applied mechanical or acoustical impingements with maximum velocity of vibrating motion. That is to say, the acoustic energy receiving surface 21 will readily accept transmitted, acoustic energy in form of wave motion, if the frequency of wave motion is equal to the inherit, natural frequency of surface 21. Experience in constructing the existing prototype device showed best results at a natural frequency of 40 KHz. In the above arrangement, the length of spacers 25 has been selected to keep the acoustical energy transmitting surface 10, and acoustic wave receiving surface 21 separated through the well define distance (d); which at a frequency of 40 KHz, and at a mean operating temperature of 20° C. was determined to be about 0.169 in., or the equivalent of ½ period of a single, full wave acoustical propagation. FIG. 2 shows a detailed block circuit diagram of the subject matter pertaining to the present invention in its preferred embodiment; in which reference number 30 is an amplitude stabilized, constant frequency oscillator, producing electric pulses of square or sign wave configuration. The oscillator produced electric output becomes the input the acoustic energy producing and transmitting subassembly 31, causing it to vibrate, and thereby transforming the electric energy into acoustical energy at transmitter frequency at fixed amplitude. The acoustical energy is transmitted in form of wave motion through air at atmospheric conditions to be received by subassembly 32, at varying amplitude, which converts the received acoustic energy to alternating electrical current at transmitter frequency of sinusoidal wave form. At this point, to satisfy the basic application (which is, to measure the density of atmospheric air), the magnitude of subassembly 32 produced output voltage may be measured, and may be calibrated to indicate the magnitude of atmospheric density expressible in mass per unit volume. To complete the computerized engine fuel control system as shown in FIG. 2, the subassembly 32 produced alternating electric current is converted by the rectifier 33 into a direct current, which in turn is converted by the analogue to digital converter 34 in to digital form. Thereby making the electric output signal of the basic atmospheric density sensing transducer compatible with the system incorporated electronic computer 35. Computer 35 reads, and measures acquired data from the air density sensing transducer subassembly 32, throttle position sensor 36, engine RPM sensor 37, and engine coolant temperature sensor 38, then matches, and correlates the multitude of occurred data with a program implanted and stored in the system incorporated electronic memory 39. According to the stored program, the computer produces, and sends a correlated electric output signals of proper magnitude and timing to controller 40; which in turn causes the engine fuel injection mechanism to produce at any throttle position the correct air/fuel mixture being tailored to concurrent driving, engine and environmental conditions. In the alternate embodiment as shown in FIG. 3, the combining of the basic air density sensing transducer 41 via suitable fluid communicative connection 43 with the engine throttle body device 42 constitutes a device for measuring the mass of engine aspirated air. The engine throttle body arrangement comprises the venturi throat 44 located substantially upstream of the throttle body incorporated throttle valve 45 and fuel injector(s) 46. In operation, engine aspirated air enters the throttle body inlet 47. As the engine aspirated air passes through the narrowest portion 48 of venturi throat 44, part of its pressure is converted to velocity accompanied by a resultant drop in pressure at the vicinity of suction port 49. The magnitude of which pressure drop is dependent on the combination of throttle valve position, engine RPM, and concurrent atmospheric conditions. The difference between atmospheric and venturi reduced pressure is sensed by the piezoelectric receiver subassembly 50 of the transducer 41; in which the principle of acoustic energy transmissibility through the intervening air between the propagating and receiving piezoelectric subassemblies 52 and 50 is, as previously described in the preferred embodiment. The reduced pressure at the venturi throat 48 and the thereby reduced pressure within chamber 51 between piezoelectric subassemblies 51 and 50 causes a small amount of ambient air at concurrent atmospheric conditions to enter via adjustable flow control valve 53 into chamber 51. The small amount of ambient air passing via tapered metering valve 54 and metering orifice 55 into chamber 51 is just sufficient, to continuously expurgate said chamber. Thereby preventing air stagnation in said chamber while maintaining a minimum of pressure difference between venturi throat 44 and chamber 51, as the pressure within said chamber follows any change in pressure at suction port 49. While the pressure between venturi throat 44 and camber 51 remains relatively equal, the relative air density at this points may change according to concurrent atmospheric conditions. It should be mentioned, that the device works equally well, if the inlet of metering the valve 53 is fluid communicative connected via suitable means to a pressure takeoff port (not being shown), located substantially upstream of venturi throat 44 within throttle body 42. The venturi type flow meter device by itself, that is to say, a device consisting of a streamlined constriction of given cross-sectional dimension within a length of suitable pipe comprising means for measuring the pressure difference generated by the conversion of fluid pressure to velocity by utilizing an differential pressure transducer which by virtue of its characteristics, depends on the measurement of a force per unit area, constitutes, a device for measuring the volumetric rate of flow. Since however, the present air density sensing transducer remains at equilibrium with atmospheric temperature, while being subject to continuous expurgation and replenishment of its internally confined air, with air at concurrent atmospheric conditions; and since the transducer output does not depend on the sensing of a force per unit area, but rather on the magnitude of acoustic energy transmissibility, the device will sense occurring changes in atmospheric density, regardless of its lower than atmospheric internal pressure. Hence the venturi tube in combination with an air density sensing transducer is considered to be an air mass-flow sensing device. The air density sensing transducer is therefore capable of continuous sampling and sensing the difference between atmospheric and the reduced pressure at suction port 49, while simultaneously sensing, and measuring changes in atmospheric density due to changes in altitude or climatic conditions.

Figure 4:
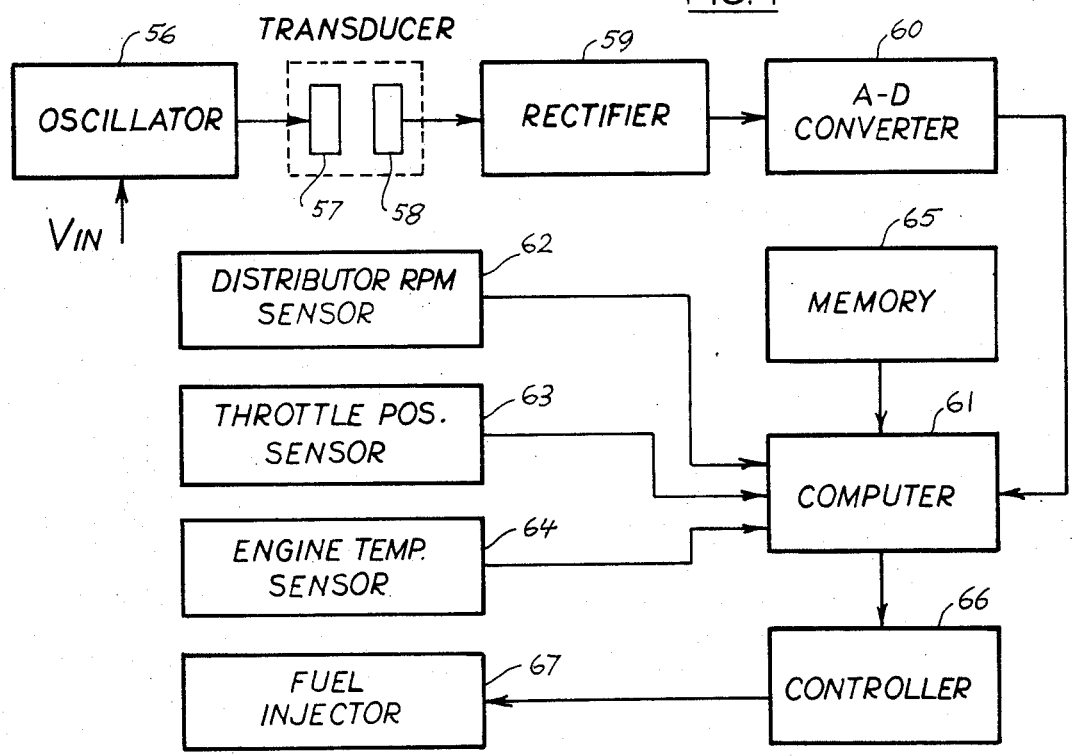
FIG. 4 represents the block circuit diagram of electronic components illustrating an alternate system for controlling the correct air/fuel mixture in internal combustion engines.

FIG. 4, represents the block circuit diagram in accordance with the alternate embodiment, in which reference number 56 is the amplitude stabilized, constant frequency oscillator, producing electric pulses of square or sinusoidal wave configuration. The output of oscillator 56 becomes the electric input to the acoustic energy producing and propagating piezoelectric transducer subassembly 57, thus causing it to vibrate and thereby convert the received electric energy to acoustical energy at the oscillator produced frequency and fixed amplitude. The acoustical energy is then propagated by subassembly 57 in form of wave motion through the air at atmospheric conditions, to be received by the acoustical subassembly 58, which in turn converts the received acoustical energy to alternating electric current at oscillator frequency and sinusoidal wave form. The magnitude of which is dependent on the concurrent density of the intervening air between the acoustic energy propagating and the receiving subassemblies 57 and 58. The subassembly 58 produced alternating electric current is received by rectifier 59, and is converted to digital form by the analogue to digital converter 60. Thereby making the air density sensing transducer produced electric output signal compatible with the system incorporated electronic computer 61. The computer 61 reads, and measures the data acquired from the air density sensing transducer subassembly 58, the distributor RPM sensor 62, the throttle position sensor 63, and the engine temperature sensor 64, then matches, and correlates the multitude of acquired data with a program implanted and stored in the computer system incorporated electronic memory 65. In accordance with the stored program, the computer produces, and sends a correlated electric signal of proper magnitude and timing to the controller 66, which in turn controls the engine fuel injector mechanism 67 to react in producing the correct air/fuel mixture to be supplied to the cylinders of the engine.

What is claimed is:

1. An acoustical device for determining the density of engine aspirated air as part of an automotive engine fuel control system comprising:
   oscillator means for providing alternating, electric current; piezoelectric, acoustic generator means for converting said alternating, electric current to acoustic energy; piezoelectric, acoustic receiver means for converting said acoustic energy to alternating, electric current; means for converting said alternating, electric current to direct current; and means for converting said direct current from analog to digital output, said components being sequentially connected to a computer including electronic means for storing engine parameter related data; said device further comprises individually connected to said computer, means for sensing engine throttle position; means for sensing distributor RPM; means for sensing engine temperature; and means for controlling the engine fuel injector;

said acoustical device comprises a first housing portion having a radially outward extending flange provided with a planar surface, and includes concentrically within disposed, said piezoelectric, acoustic wave generator means having electric input leads, and being provided with an acoustic energy generating surface disposed in a coplanar relationship with said planar surface; said acoustical device further comprises a second housing portion having a radially outward extending flange provided with a planar surface, and includes concentrically within disposed, said piezoelectric, acoustic wave receiver means having electric output leads, and being provided with an acoustic energy receiving surface disposed in a coplanar relationship with said planar surface; said first and said second housing portions are coaxial aligned so that said acoustic energy generating and said acoustic energy receiving surfaces face each other through a well defined distance being fixed by suitable means to combine said first and said second housing portions so as to expose said acoustic energy generating and said acoustic energy receiving surfaces to atmosphere;

a method wherein said piezoelectric, acoustic wave generator means receives electric pulses of a fixed frequency and amplitude, thereby stimulating said acoustic energy generating surface to produce acoustic energy in form of wave motion which is received by said acoustic energy receiving surface; wherein the acoustic energy transmissibility varies as the density of intervening air between said acoustic energy generating and said acoustic energy receiving surfaces; wherein the magnitude of electric output of said piezoelectric, acoustic wave receiver means is proportional to the density of said intervening air;

and wherein the magnitude of said piezoelectric, acoustic wave receiving means produced electric output, together with the electric output produced by said means for sensing throttle position, said means for sensing distributor RPM, and said means for sensing engine temperature are continuously computed and correlated by said computer with said stored data, to compensate by readjusting said engine fuel injector to constantly occurring changes in engine throttle position, engine load, and engine environmental conditions.

2. An acoustical device for determining the density of engine aspirated air in combination with a flow sensing means as part of an automobile fuel control system comprising:

oscillator means for producing alternating, electric current of fixed frequency and amplitude;

first piezoelectric element for receiving and converting said oscillator produced alternating current to acoustic pressure pulses;

second piezoelectric element for receiving and converting said acoustic pressure pulses into alternating, electric current;

means for converting said alternating, electric current to direct current; and means for converting said direct current to digital output; said components being sequentially connected to a computer including electronic means for storing engine parameter related data; and further comprises means for sensing engine throttle position, means for sensing distributor RPM, means for sensing engine temperature, and means for controlling the engine fuel injector, said components are individually connected to said computer;

said fuel control system further comprises flow sensing means; said acoustical device comprising housing means having a cavernous interior defined by cylindrical inner wall and opposite disposed end walls, said cavernous interior comprises internally disposed said first and said second piezoelectric element; said first piezoelectric element having electric input leads and an acoustic energy generating surface; and said second piezoelectric element having electric output leads and an acoustic energy receiving surface being spaced, and facing said acoustic energy generating surface through a well defined distance to form a chamber defined by portion of said cylindrical inner wall, said acoustic energy generating and said acoustic energy receiving surface;

said acoustic energy generating surface and said acoustic energy receiving surface being characterized by having the same, inherent, natural frequencies of vibration; said housing further comprising fluid communicative inlet and outlet ports; said inlet port comprises metering adjustment means, characterized by its ability to adjust for fluid flow; said outlet port being fluid communicatively connected via suitable means to said flow sensing means;

said flow sensing means comprises tubular means having axially disposed fluid inlet and fluid outlet apertures, and internally disposed flow constriction provided with fluid communicative connection from the narrowest portion of said constriction to an externally disposes port, being fluid communicatively connected via suitable means to said outlet port of said housing means;

a method wherein in operation said first piezoelectric element is stimulated by the electric output of said oscillator means to produce acoustic energy in form of wave motion, and wherein said acoustic energy is received at varying amplitude by said second piezoelectric element, and is thereby converted into alternating, electric current, whose magnitude changes as the density of intervening air between said acoustic energy generating surface and said acoustic energy receiving surface; and wherein, as air passes through said fluid flow sensing means, air pressure is converted to velocity, resulting in a proportional drop in pressure within said constriction, accompanied by an equal pressure drop within said chamber; and wherein said pressure drop within said chamber causes a small amount of ambient air controlled by said adjustment means to enter said chamber, in which the acoustic energy transmissibility from said first to said second piezoelectric element is proportional to the density of intervening air between said acoustic energy generating surface and said acoustic energy receiving surface; whereby, the electric output of said second piezoelectric element is proportional to the velocity of air through said constriction, which, together with the density within said chamber produces the mass-flow rate of engine aspirated air; said mass-flow rate may change at any engine load and/or throttle position, as the density of said small amount of air entering said chamber at concurrent atmospheric conditions.

3. Acoustic device for measuring the density of air, comprising: housing means having cavernous interior, and having at least one fluid communicative passageway from said interior to atmosphere; piezoelectric, acoustic wave generator means, and a substantially identical piezoelectric, acoustic wave receiver means; said housing means comprises a first portion having a radially outward extending flange provided with a planar surface, and includes concentrically within disposed said piezoelectric, acoustic wave generator means having electric input leads, and being provided with an acoustic wave generating surface disposed in coplanar relationship with said planar surface; said housing means further comprises a second portion having a radially outward extending flange provided with a planar surface, and includes concentrically within disposed said piezoelectric, acoustic wave receiver means having electric output leads, and being provided with an acoustic wave receiving surface disposed in coplanar relationship with said planar surface; said first and said second housing portions being coaxial aligned so that said wave generating and said wave receiving surfaces face each other through a well defined distance along the longitudinal path of wave propagation, and being fixed by suitable means to combine said first and said second housing portion so as to expose said wave generating and said wave receiving surface to atmosphere; said acoustic device further comprises crystal controlled oscillator means for driving said wave generator means, hereby propagating acoustic energy in form of longitudinal wave motion to be received by said wave receiving means, and to generate alternating current whose voltage changes as the density of air within said device.

* * * * *